(12) United States Patent
Xie

(10) Patent No.: US 11,682,472 B2
(45) Date of Patent: Jun. 20, 2023

(54) AUGMENTED AND VIRTUAL MIXED REALITY METHODS AND SYSTEMS FOR PHARMACEUTICAL AND MEDICAL RESEARCH, DEVELOPMENT, AND EDUCATION

(71) Applicant: Xiang-Qun Xie, Mars, PA (US)

(72) Inventor: Xiang-Qun Xie, Mars, PA (US)

( * ) Notice: Subject to any disclaimer, the term of this patent is extended or adjusted under 35 U.S.C. 154(b) by 423 days.

(21) Appl. No.: 16/639,966

(22) PCT Filed: Aug. 27, 2018

(86) PCT No.: PCT/US2018/048139
§ 371 (c)(1),
(2) Date: Feb. 18, 2020

(87) PCT Pub. No.: WO2019/040936
PCT Pub. Date: Feb. 28, 2019

(65) Prior Publication Data
US 2022/0172797 A1 Jun. 2, 2022

Related U.S. Application Data

(60) Provisional application No. 62/550,268, filed on Aug. 25, 2017, provisional application No. 62/550,162, filed on Aug. 25, 2017.

(51) Int. Cl.
*G16B 15/00* (2019.01)
*G16C 60/00* (2019.01)
(Continued)

(52) U.S. Cl.
CPC ......... *G16B 15/00* (2019.02); *G06F 3/04815* (2013.01); *G06T 19/20* (2013.01);
(Continued)

(58) Field of Classification Search
CPC ..... G16B 15/00; G06F 3/04815; G06T 19/20; G06T 2219/2016; G09B 9/00; G16C 60/00
See application file for complete search history.

(56) References Cited

U.S. PATENT DOCUMENTS

2011/0213625 A1* 9/2011 Joao ................. G16H 20/40
705/2
2014/0340999 A1* 11/2014 Zhang ................ G04G 21/04
368/109
(Continued)

*Primary Examiner* — Jitesh Patel
(74) *Attorney, Agent, or Firm* — Dentons Cohen & Grigsby P.C.

(57) ABSTRACT

Systems and methods to provide augmented and virtual reality implementations of information sources useful as learning and discovery tools are disclosed. A computer implemented method and programming product which provides enhanced visualization of various information resources useful for at least teaching and learning, drug research and discovery, and precision and personalized medicine. A computer-implemented method and programming product for providing medication and/or appointment reminder, alerts, and education is also provided. These cross platform software applications use graphic processing unit (GPU) accelerated big data analysis algorithms, and innovative natural language processing (NLP) algorithms to improve user experiences and access to the information resources.

22 Claims, 7 Drawing Sheets

(51) Int. Cl.
*G06F 3/04815* (2022.01)
*G06T 19/20* (2011.01)
*G09B 9/00* (2006.01)

(52) U.S. Cl.
CPC ............... *G09B 9/00* (2013.01); *G16C 60/00* (2019.02); *G06T 2219/2016* (2013.01)

(56) References Cited

U.S. PATENT DOCUMENTS

| | | |
|---|---|---|
| 2015/0269855 A1 | 9/2015 | McGill |
| 2016/0225192 A1* | 8/2016 | Jones ........................ G06T 19/20 |
| 2016/0249989 A1 | 9/2016 | Devam et al. |
| 2017/0076055 A1* | 3/2017 | Minemura ............. G16H 10/60 |
| 2017/0213473 A1* | 7/2017 | Ribeira ................... G06T 13/40 |
| 2019/0392936 A1* | 12/2019 | Arric ........................ A61J 1/03 |

* cited by examiner

FIG. 8A  FIG. 8B  FIG. 8C

AUGMENTED AND VIRTUAL MIXED REALITY METHODS AND SYSTEMS FOR PHARMACEUTICAL AND MEDICAL RESEARCH, DEVELOPMENT, AND EDUCATION

CROSS REFERENCE TO RELATED APPLICATIONS

This application is a U.S. national stage filing under 35 U.S.C. § 371 of International Application No. PCT/US2018/048139 filed on Aug. 27, 2018 entitled "Augmented and Virtual Mixed Reality Methods and Systems for Pharmaceutical Research, Development, and Education", which claims priority to U.S. Provisional Application No. 62/550,268 filed on Aug. 25, 2017 entitled "Augmented and Virtual Reality Methods and Systems for Medical Research, Development, and Education" and U.S. Provisional Application No. 62/550,162 filed on Aug. 25, 2017 entitled "Personalized Medical Tracking and Reminder Application,". The foregoing applications are incorporated as though set forth herein in their entirety.

TECHNICAL FIELD

This invention pertains generally to interactive learning, and pharmaceutical and medical health care tools, and more specifically to software applications that may provide augmented reality assisted learning aids and personalized medication scheduling, information, and education.

BACKGROUND

Modern electronic devices are becoming increasingly powerful and sophisticated. Not only are these devices running faster central processing units (CPUs), they are also equipped with enhanced graphics abilities through faster graphic processing units (GPUs) and often include sensors such as global positioning systems (GPS), gyroscopes, and accelerometers that are making these devices more versatile and have opened up a world of applications that did not seem possible before.

One example is virtual reality (VR), which is a computer technology that uses software-generated realistic images, sounds, and other sensations to replicate a real environment or an imaginary setting, and simulates a user's physical presence in this environment to enable the user to interact with this space. Another example, augmented reality (AR), provides live direct or indirect viewing of a physical real-world environment whose elements are augmented (or supplemented) by virtual computer-generated sensory input such as sound, video, graphics, or GPS data. And finally, mixed Reality (MR) is the merging of real and virtual worlds to produce new environments and visualizations where physical and digital objects co-exist and interact in real time.

Virtual, augmented and mixed reality applications have traditionally been limited to expensive custom computer setups generally used only in universities and academia. With the advent of modern devices that include powerful embedded processors, many of the algorithms that were once confined to large static computer setups are becoming a part of the mobile world. All of these new technologies, however, are CPU and GPU intensive.

As such, there exists a need in the art for augmented and virtual reality implementations of information resources on mobile devices, and improvements in the computational and graphics speeds and capabilities of such implementations.

These modern electronic devices may also provide a platform for other expanded capabilities previously restricted to static computer setups. For example, there exists a need in the art for improved methods of managing medication and medical appointments and for providing increased access to medical news and information.

Avoiding unnecessary medical complications or death by ensuring a drug is efficacious for the patient and that the patient is compliant and persistent with their prescription(s) represents a major unmet need. According to Express Scripts, the largest pharmacy benefit manager in the United States, only 25 to 30 percent of medications are taken according to the prescriber's instructions, and of those taken, only 15 to 20 percent are refilled according to the prescriber's instructions. This lack of adherence and persistence is estimated to result in excess of $300 billion being wasted annually for the treatment of unnecessary medical complications in the United States.

Periodic evaluation of a patient's drug regimen is an essential component of medical care. However, a survey of Medicare beneficiaries found that more than 30 percent of patients reported they had not talked with their doctor about their different medications in the previous 12 months. Furthermore, when these reviews are done, they often ignore over-the-counter medications and supplements, herbal medications, and recreational drugs that are being taken by the patient.

Multiple factors contribute to the appropriateness and overall quality of drug prescribing. These include avoidance of inappropriate medications, appropriate use of indicated medications, monitoring for side effects and drug levels, avoidance of drug-drug interactions, and involvement of the patient and the patient's biometric and health values. Current measures of the quality of prescribing generally focus on one or some of these factors, but rarely on all.

Thus, a software application accessible on a mobile electronic device that may educate and assist in managing a patient's medications and medical appointments would fulfill an unmet need in the art.

SUMMARY

The presently disclosed invention is related to software applications that expand upon prior art methods of delivering and interacting with information resources. To overcome the hardware challenge in computing "big-data" type databases or libraries, the present invention may incorporate programming of the GPU (e.g., CUDA, DirectX, or OpenCL) to enhance the computational performance over CPU code alone. Moreover, the present invention may provide software applications that work across a range of platforms (i.e., cross platform software applications).

The presently disclosed invention provides a software application that delivers various information and data sources as augmented and virtual reality implementations of learning and discovery tools. The presently disclosed invention also provides a software application that delivers information and data sources useful as reminder tools, providing enhanced means to receive, interact with, and manage various medical and medication related information. For example, the presently disclosed invention provides a software application useful to remind a user to take and refill medications learn about current news regarding their medications, and/or schedule and attend medical appointments in a timely manner According to its major aspects, and briefly stated, the presently disclosed invention includes a computer-implemented method for providing an augmented or virtual reality learning tool. The presently disclosed invention also includes a method for providing an augmented or virtual reality learning application, wherein the application may be executed by one or more processors. The presently disclosed invention also includes a method for providing an augmented or virtual reality learning application, wherein the application is stored on a non-tangible computer readable medium tangibly embodying non-transitory computer-executable program instructions thereon that, when executed, cause a computing device to execute or perform the method.

The method may comprise decoding a request for a data set related to a target stored on an information server; accessing, by a mobile internet device via a wired or a wireless network, the information server; importing the data set from the information server; extracting spatial information from the data set; and displaying a spatial image on the mobile internet device, wherein the spatial image is based on the spatial information.

According to certain aspects, the spatial information may comprise a digital representation of an arrangement of the target in a physical environment. The target may be an organ, a skeleton, a body, a nervous system, a digestive system, a circulatory system, or a combination thereof. The target may be a molecule, such as a protein molecule, a DNA molecule, a peptide, a drug, or a combination thereof. The target may be an organ comprising a single organ, multiple organs, or an entire body.

According to certain aspects, exemplary mobile internet devices include at least: a game device, a smart phone, a tablet, a camera, a robot, an augmented or virtual reality viewer, and a watch. The data set may be imported to the mobile internet device, or the data set may be imported to a server which carries out the step of extracting the spatial information from the data set. The extracted spatial information may be sent to the mobile internet device via either a push or pull from the server.

According to certain aspects, the method may further comprise altering the spatial image on the mobile internet device based on user commands, wherein the user commands comprise moving the spatial image, resizing the spatial image, rotating the spatial image, deleting part of or all of a spatial image, and stretching the spatial image, and combinations thereof.

According to certain aspects, a spatial image may be generated for a second target, and the method may further include altering the spatial image of the first and second targets on the mobile internet device based on user commends. Such may be done to dock molecules relative to one another, such as a drug molecule docked within a binding site on a protein, or to dock an organ within a larger system of a body, such as docking internal organs in their proper locations in a body cavity.

The presently disclosed invention further includes a system for providing an augmented or virtual reality learning tool, the system comprising a processor and a memory containing instructions that, when executed by the processor cause the processor to execute or perform the methods for providing an augmented or virtual reality learning tool disclosed herein. According to certain aspects, the processor and/or memory may be part of a virtual reality device, or may be part of a mobile electronic device configurable to display or interact with a display or virtual reality device.

The presently disclosed invention further includes a computer implemented program product for providing an augmented or virtual reality learning tool, comprising a non-tangible computer readable medium tangibly embodying non-transitory computer-executable program instructions thereon that, when executed, cause a computing device to execute or perform the methods for providing an augmented or virtual reality learning tool disclosed herein.

According to its major aspects, and briefly stated, the presently disclosed invention also includes a computer-implemented method for providing a medication and/or appointment reminder, and/or medication educator. The presently disclosed invention also includes a method for providing a medication and/or appointment reminder and/or medication education application, wherein the application may be executed by one or more processors. The presently disclosed invention also includes a method for providing a medication and/or appointment reminder and/or medication education application, wherein the application is stored on a non-tangible computer readable medium tangibly embodying non-transitory computer-executable program instructions thereon that, when executed, cause a computing device to execute or perform the method.

The method may comprise connecting to an information server via an internet protocol network; acquiring stored patient information from the information server, wherein the stored patient information comprises a medication to be taken by a patient and a dose schedule; starting a timer associated with the dose schedule; and activating an alert or alarm at a time interval defined by the dose schedule.

The stored patient information may comprise a set of patient specific data, wherein the set of patient specific data may comprise at least a patient name, a medication identification, and a medication dosing schedule. The patient specific data may be obtained via direct input by the patient or user, and/or from a medical database maintained by the patient's or user's pharmacy or medical facility (e.g., primary care physician, hospital or medical facility, etc.), or may be information encoded on the medication (e.g., barcode or QRcode). The set of patient specific data may further comprise a patient age, a patient weight, a patient height, a patient blood pressure, a patient cholesterol, a patient insulin level, a patient blood sugar level, a patient heart rate, a patient temperature, or any combination thereof.

The method may further comprise acquiring the stored patient information from a second server having stored thereon current values for a patient age, a patient weight, a patient height, a patient blood pressure, a patient cholesterol, a patient insulin level, a patient blood sugar level, a patient heart rate, a patient temperature, or any combination thereof. This set of patient specific data may be used to determine a change to the dose schedule, or a health message regarding the dose schedule.

According to certain aspects, the stored patient information may further comprise an appointment schedule; and the method may further comprise starting a timer associated with the appointment schedule; and activating an alert or alarm at a time interval defined by the appointment schedule.

The presently disclosed invention also provides a system for providing a medication and/or appointment reminder, the system comprising a processor; and a memory containing instructions that, when executed by the processor, cause the processor to perform the method as detailed above.

The presently disclosed invention also provides a computer implemented program product for providing a medication and/or appointment reminder, the program product comprising a non-tangible computer readable medium tangibly embodying non-transitory computer-executable program instructions thereon that, when executed, cause a computing device to execute the method steps as detailed above.

BRIEF DESCRIPTION OF THE DRAWINGS

Aspects, features, benefits and advantages of the embodiments herein will be apparent with regard to the following description, appended claims, and accompanying drawings. In the following figures, like numerals represent like features in the various views. It is to be noted that features and components in these drawings, illustrating the views of embodiments of the presently disclosed invention, unless stated to be otherwise, are not necessarily drawn to scale.

FIGS. 8A-8C illustrate exemplary screen views (iPhone) of a medication and appointment reminder interface of a software application in accordance with certain aspects of the presently disclosed invention;

DETAILED DESCRIPTION

Figure 1:
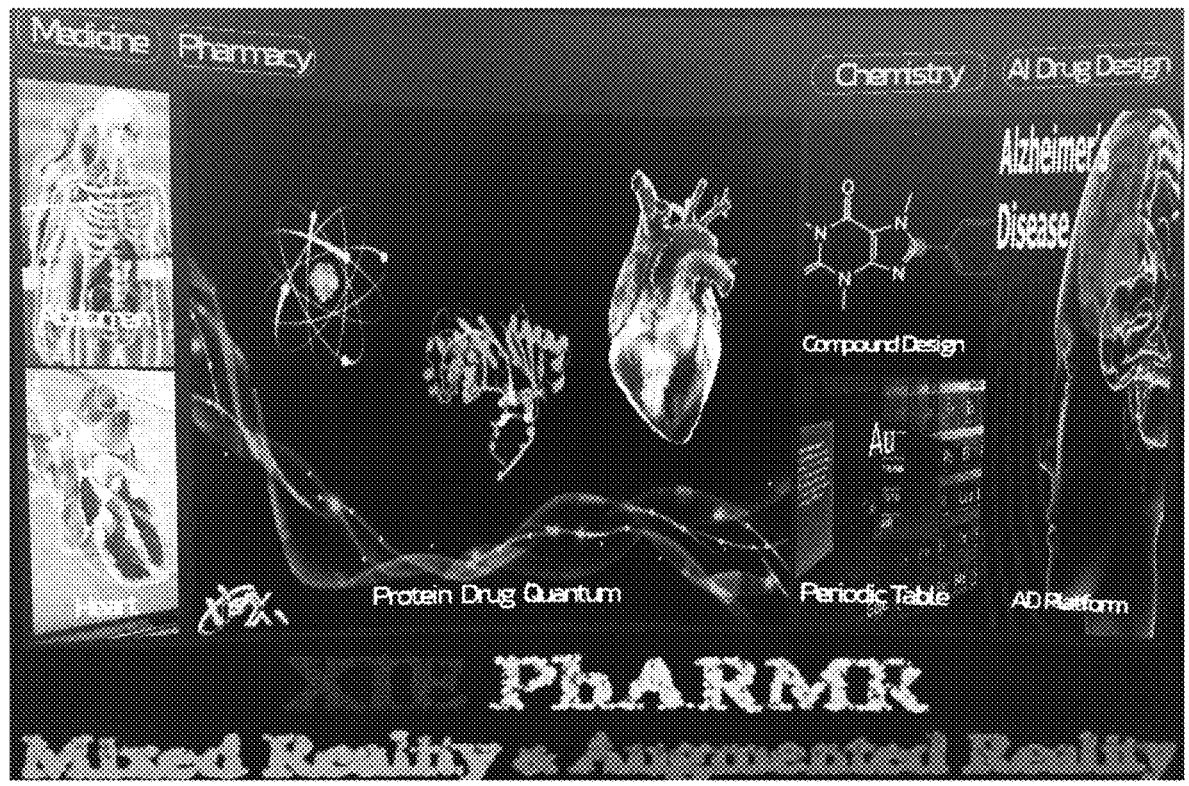
FIG. 1 illustrates a screen shot taken from a VR/AR/MR application portal according to certain aspects of the present invention in pharmaceutical and medical R&D and education.

In the following description, the present invention is set forth in the context of various alternative embodiments and implementations involving augmented and virtual reality methods and systems which provide novel learning and discovery tools. The present invention is also set forth in the context of various alternative embodiments and implementations involving a personalized medical tracking and reminder software application. While the following description discloses numerous exemplary embodiments, the scope of the present patent application is not limited to the disclosed embodiments, but also encompasses combinations of the disclosed embodiments, as well as modifications to the disclosed embodiments.

Various aspects of the systems and methods may be illustrated by describing components that are coupled, attached, and/or joined together. As used herein, the terms "coupled", "attached", and/or "joined" are interchangeably used to indicate either a direct connection between two hardware components, or two software modules, or, where appropriate, an indirect connection to one another through intervening or intermediate components or modules. In contrast, when a component is referred to as being "directly coupled", "directly attached", and/or "directly joined" to another component or module, there are no intervening elements shown in said examples.

Various aspects of the systems and methods may be described and illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to".

It must also be noted that as used herein and in the appended claims, the singular forms "a", "an", and "the" include the plural reference unless the context clearly dictates otherwise. Unless defined otherwise, all technical and scientific terms used herein have the same meanings as commonly understood by one of ordinary skill in the art.

The present invention provides software applications configured to work across many platforms (e.g., Android, iOS, Microsoft Windows, etc.) to provide (1) augmented and virtual reality implementations of information resources useful as learning and discovery tools, and (2) personalized medical and medication tracking, e.g., remind a user to take and refill medications, or to schedule and attend medical appointments in a timely manner. The presently disclosed software applications may use programming of the graphics processing unit (e.g., CUDA, DirectX or OpenCL) to enhance the computational performance over CPU code alone. Moreover, an innovative natural language processing (NLP) algorithm may be included which may assist the user to interface with the software applications. For example, the NLP may assist the user to educate themselves with the latest news regarding their medications, medical conditions, and healthcare advances in general, as well as common information on drug use and abuse.

The information displayed may be used for educational purposes. For example, medical information such as images of organs, body systems, or even whole bodies may be used in medical training and education applications. Three-dimensional structural information of molecules, such as proteins, peptides, DNA molecules, drugs, etc., may be used for educational or research and development purposes. Structural three dimensional (3D) representations of the human body, or body systems or organs, may be useful in precision and personalized medicine.

In conjunction with pharmacy, insurance, medical, or IT facilitates and/or companies, the presently disclosed software applications may be configured to accept and utilize updated information sources, programming algorithms, and patient output formats to provide an enhanced user experience.

According to certain aspects, the presently disclosed software application may facilitate the Pharmacy-to-Patient process. For example, the barcode or QRcode commonly incorporated into the packaging of a medication or supplement may include additional information with encryption algorithms that can be either pushed to or scanned by a patient's or user's mobile device to manage (pick up, take, refill, etc.) their medications. Moreover, the patient or user may use the software to consult with the Pharmacy regarding requests for additional information, scheduling changes and/or advice, refill requests, etc.

The presently disclosed software applications may further be used to assist in drug abuse avoidance. For example, based on the big data analysis algorithm which is part of the disclosed software application, the software application may suggest the optimum plan to the patient or user. Patients or users may also be provided with, or actively seek out through a search function, the latest news and/or common information on drug abuse to avoid such a problem through the natural language processing (NLP) algorithm.

The presently disclosed software applications may further be able to accelerate and strengthen the evolution of media and human communication. For example, according to certain aspects, the application may function across many platforms, and may be connectable to external devices, such as health and/or fitness trackers (Apple Watch, Jawbone, Fitbit, Body Cardio, etc.) for health data access and management. The presently disclosed software applications may be used to obtain first-hand health data from the health or fitness tracker for the patient or user which may include, but is not limit to, a user id (generated by the external device health or fitness tracker application), age, sex, medications, weight, temperature, heart rate, blood pressure (Body Cardio, Nokia), etc.

Following is a description of the various components and potential uses of the methods and systems of the present invention. While specific examples of information resources are provided, such should not be taken as a limitation on the range or scope of the type of information that may be displayed or presented using the systems and methods of the presently disclosed invention.

I. VR/AR/MR applications for modeling, education, and training

Data loading and organization/arrangement: According to certain aspects, a system and method of the presently disclosed invention may be generally described as an innovative three-dimensional (3D) computing program platform which is powered by virtual reality/augmented reality/mixed reality (VR/AR/MR) devices. The program is generated using a suite of scripts/codes to load and visualize a range of information subject(s), such as a biological molecule from a file format, such as including PDB, mol/mol2, and others; and chemical molecules or atoms (orbital and electronics), etc.; and organs or whole bodies, such as a human vasculature or set of organs.

As used herein, the term "biological molecule" refers to the sequence of nucleotide or amino acid residues of a biological molecule (e.g., a DNA molecule, an RNA molecule, a polypeptide, a carbohydrate, or a lipid). A biological molecule or sequence can be graphically represented structurally, such as a chemical structure, a ball-and-stick model, a ribbon diagram, a space-filling model, an electrostatic model, etc.; or any combination thereof.

Further, data associated with organs, such as 3D imaging data (e.g., data from MM, CAT scan, ultrasound, tomography, etc.), may be used as input. Such a process is accelerated by the GPU-computing algorithms of the presently disclosed software application.

The programs may generally be configured to (1) decode the subject(s)/data (molecules, atoms, organs, etc.); (2) import basic information/subject(s) (including but not limited to atom, chain, molecule, organ, etc.); (3) extract useful information/subject(s) (including but not limited to protein sequence, residue, $\alpha$-helix, $\beta$-sheet, and random coil, ligand/inhibitor/substrate etc.); (4) organize/arrange/select the info/subjects and properties in hierarchy so that the program can display the subject(s) properly, such as 3D structure of protein/DNA/small molecule/other object correctly.

For protein targets, for example, the "PDB" (protein data bank) may store data sets related to the spatial information for individual protein chains, molecules, subunits, etc. The PDB is actually the primary repository for all published protein and nucleic acid (macromolecular) 3D structures. Parsing code for PDB structures may be found in different open resources, and may be included in the present GPU-accelerated platform along with computing algorithms, program functions/codes to enhance visualization of the targets. For small molecules, data sets related to the spatial information for individual atoms may be found, for example, in a number of chemistry databases, including NCI Web-Accessible Data; Computational Chemistry Comparison and Benchmark DataBase (CCCBDB); ChemIDplus; SOLV-DB; Common Compound Library; ChemFinder; etc.

Moreover, the data sets for biological molecules or certain small molecule targets may be derived from spatial data from structure prediction algorithms. Certain of these structures are calculated and stored in additional repositories, such as SWISS-MODEL which is a Repository is a database of protein structure homology models generated by the fully automated SWISS-MODEL modeling pipeline; or the Protein Model Portal which provides access to structural information for a protein—both experimental structures and theoretical models (Protein Model Portal is a component of the Nature PSI Structural Biology Knowledgebase); or any of the other databases or prediction algorithms disclosed in the ExPASy Bioinformaticcs Resource Portal.

According to certain aspects, the software application of the presently disclosed invention, the data sets for certain objects (i.e., organs, body systems, or a body) may be derived from optical images, or alternatively may be captured by means of an alternative non-optical imaging modality, such as but not limited to X-ray, magnetic resonance imaging (MRI), ultrasound or the like, that allows for capturing one or more images of a portion of the object or the object in its entirety (including, for example, any portions that may be embedded within the object). The imaging modality through which the 3D model is reconstructed may be a tomographic imaging modality such as but not limited to a CT scan, a PET scan, a tomographic MRI, an ultrasound tomography or the like. According to certain aspects of the invention, the 3D model may be periodically updated, with imaging sessions interspersed between, or performed concurrently with, viewing using the methods and system of the present disclosure. Periodically updating the construct model may be advantageous in cases where the shape or other features of the object changes over time, for example through manipulation of the object by a person.

Alternatively or additionally, 3D model may include added visual content that is not a representation of physical features of a corresponding object (e.g., biological molecule, organ, body, etc.) or region thereof, but provides information about the object or region. The visual content may be, for example, a piece of text such as a symbol, a name, a description, or a parameter (for example, binding site on a protein for a drug, name of region on the protein, name of an organ, etc.), Alternatively or in addition, the added visual content may be a graphic, for example an expected trajectory of the object, a planned placement or path of a non-existing object, a flashing circle highlighting the object/region or the like. Alternatively or in addition, the added visual content may be a video stream, for example show binding of a drug to a protein, dissipation of a drug within an organ, etc. Many other added types of visual content may occur to a person skilled in the relevant art.

According to certain aspects, the software application of the presently disclosed invention executing upon a computing device may access a remote server (e.g., via a network) to conduct a portion of the operations to achieve the augmented or virtual display presented within the display of the AR/VR/MR device. For example, the software application executing upon the computing device may receive all or a portion of the data (data sets related to the spatial information of the target) from a remote server. The software application may then pass all or a portion of the data (data sets related to the spatial information of the target) to another remote server, or may process the information on a local server.

According to certain aspects, the software application executing upon the computing device may pass user configuration settings (e.g., as saved in a configuration data storage), user inputs, or other data to the server. Configuration settings may include any or all of a user identification, user preferences regarding sizing, color, orientation, etc. of a displayed model, user preferences regarding devices and output characteristics, user preferences regarding manipulation means, speeds, types, etc. for the displayed model, etc.

Subject visualization: Information sources which may be displayed using the systems and methods of the presently disclosed invention include at least protein or peptide/DNA or RNA/small molecule visualization, atomic orbital/electron cloud visualization, and organ or whole body visualization.

For example, the program may display biological or small molecules in different ways ("Wireframe", "Stick", "ball", "Ball-Stick", "Cartoon", "Surface", "Sequence", etc.), which may be attached with the name/selection of each component, using VR/AR/MR devices and a downloaded version of the presently disclosed software application, which may function on various computer platforms, such as Mac, Window, Android, iOS, etc.

A Function/Subject Selection Panel may be included to allow users to change or combine the display modes. The software application may be configured to visualize the interactions between receptors and ligands (such as H-bonding, van der Waals interactions, charge interaction and hydrophobic interactions). Multiple display modes may be used at one time in order to present different functions/attributes of a molecule or a portion of a molecule. Basic 3D operation (Translate/Rotate/Scale/MousePick) may be supported. In addition, the software application may be configured to provide analysis and display of Pocket(s) and Pharmacophore(s) of the molecule, and display in solid, transparent, or dotted modes.

Medical information such as images of organs, body systems, or even whole bodies may be displayed based on 3D imaging data. This data may include single organs, clusters of organs, specific systems of the body or graphic models stored on an information server (circulatory system, digestive system, nervous system, skeletal system, etc.), or the whole body. Thus, information may be displayed singly, may be overlaid, and/or may be highlighted per the user's request, and based on the specific functionality of the application (e.g., discovery, education, mock surgery, etc.).

The various application programs of the present invention may be accessible via an internet connection on a remote server, or may be converted to user applications which may be downloadable to allow usage by various platforms, including but not limited to PC/Mac/Unix/Linux computers/workstations, phones (iPhone, google and Android) and iPad or other tablet or portable device usages.

The presently disclosed invention further provides for integration of basic and advanced functions and algorithms of the VR/AR/MR devices (basic gaze, gesture, sound such as voice, spatial mapping). For example, the VR/AR/MR devices generally have functions which include, but are not limited to: i) Use of a cursor to display the user's gaze (cursor on/off holograms, directional indication, etc.); ii) Gesture for hand detected feedback (zoom in/out, rotation, hand manipulation, etc.); and iii) Spatial sound and Spatial mapping (Scan the environment and transfer data from HoloLens to computer, etc.). The presently disclosed invention integrates all of or a subset of these functionalities.

Thus, the presently disclosed invention may provide methods for drug discovery and education, which may be compatible to VR/AR/MR devices; and/or mobile devices such as mobile phones. The presently disclosed invention may also provide methods for discovery and education in the area of surgery and body function/structure, which may be compatible to VR/AR/MR devices; and/or mobile devices such as mobile phones.

In order to direct dynamic selection and/or visualization of the user selected data set (e.g., protein), the VR/AR/MR device may track the user's view position in which an imaginary ray is projected that corresponds to the user's line of sight (i.e., the direction in which the user is looking). The tracked view position is utilized to determine whether the user is interacting with a virtual display or making additional selections. The VR/AR/MR device may be configured to control the virtual display responsive to audible commands recognized via a microphone, and/or hand gesture commands recognized via a camera, and/or eye gesture commands recognized via a camera.

The types of commands and the way that such commands control the 3D model may vary without departing, from the scope of this disclosure. To create a virtual display for dynamic interaction with the 3D model, for instance, a forward-facing camera may recognize a user's left and/or right hands, and certain gestures that a user may make with their hand(s). These gestures may translate to certain responses from the software application. For example, the user may make a stop-sign hand gesture to pause playback, swipe a hand from left to right to fast forward, or twist an outstretched hand to change a channel. The user may grasp regions of the displayed model to move, rotate, or resize the model. These hand gestures may be combined or used in addition to certain vocal commands. For example, a user may speak commands such as "pause," "fast forward," "rotate," "shrink," etc. to control display of the 3D model, or a rate of rotation or movement of the 3D model. As another example, a user may speak "split" or make a karate chop gesture to split a single virtual monitor into two virtual monitors.

Testing on various devices: The presently disclosed invention underwent beta-version testing and user evaluation on a HoloLens device. Users were presented with subjects such as biological molecules (e.g., protein/DNA/ small molecules), inorganic molecules, atoms/electrons, and human body/organs, in a 3D scene through HoloLens glasses and were allowed to dynamically operate (move, rotate, etc.) each molecule through gaze or gesture. The presently disclosed application may be installed and run on multiple different platforms (cross-platform), including mobile devices such as iOS, Android, Microsoft windows phone, etc.

The HoloLens device is a head mounted VR/AR/MR display device operable by a user in a physical environment. Such devices generally comprise a display configured for rendering a VR/AR/MR environment to the user, wherein a view position of the user for the rendered VR/AR/MR environment may be variable depending at least in part on a pose of the user's head in the physical environment. According to certain aspects, the VR/AR/MR display device may include one or more processors; a sensor package; and one or more memory devices storing computer-readable instructions which, when executed by the one or more processors, perform a method comprising the steps of: rendering a three-dimensional (3D) virtual display. According to certain aspects, the processors and memory may be part of a secondary computing device, such as a user's mobile electronic device, or may be part of a static computing device configured to communicate with the VR/AR/MR display device via a wired or wireless communication. Thus, the VR/AR/MR display device may further include a network interface for receiving data from a remote computing platform over the network interface. As such, the VR/AR/MR display device may act as a display device only, or may include computing capability.

According to certain aspect, the method may include rendering the 3D model as a hologram in the display of the VR/AR/MR device. In another example, the method further includes dynamically updating the rendered hologram on the VR/AR/MR device responsively to the user inputs. In another example, the method further includes obtaining sensor data from a sensor package of the VR/AR/MR device, the sensor data associated with a physical environment adjoining a user of the VR/AR/MR device; and, using the sensor data, reconstructing a geometry of the physical environment including any real world object located therein.

In another example, the sensor data includes depth data and the sensor data is generated using a depth sensor and surface reconstruction techniques are applied to reconstruct the physical environment geometry. A further examples includes a method performed by the VR/AR/MR device supporting a mixed-reality environment including virtual objects and real objects, the method comprising implementing a virtual 3D space or environment on a display of the VR/AR/MR device into which the 3D model of the target is positioned or displayed.

EXAMPLES

With reference to FIGS. 1-7B, the presently disclosed invention may provide a VR/AR/MR software application based on an innovative means to display and interact with a range of different information sources. Following is a list of specific examples of the systems and methods of the presently disclosed invention.

(1) GPU accelerated cloud computing big/health data technology for cross-platform innovative discovery applications:

The presently disclosed invention may provide a comprehensive drug discovery platform that includes integrated GPU accelerated cloud computing big/healthy data technology. Shown in FIG. 1 is an exemplary portal to the software application that may be provided to a user on a VR/AR device or standard display for a computing device. The presently disclosed cross-platform software application may provide users with a variety of information sources and means to interact with the information sources. For example, with reference to FIG. 1, the portal may provide 3D visualization of organs or portions of a human body, as shown at left; or proteins and 3D models for drug discovery, drug pharmokinetics, etc., as shown in the center; or molecules or atoms as shown at right; or specific disease models and information, as shown at the far right.

Figure 2:
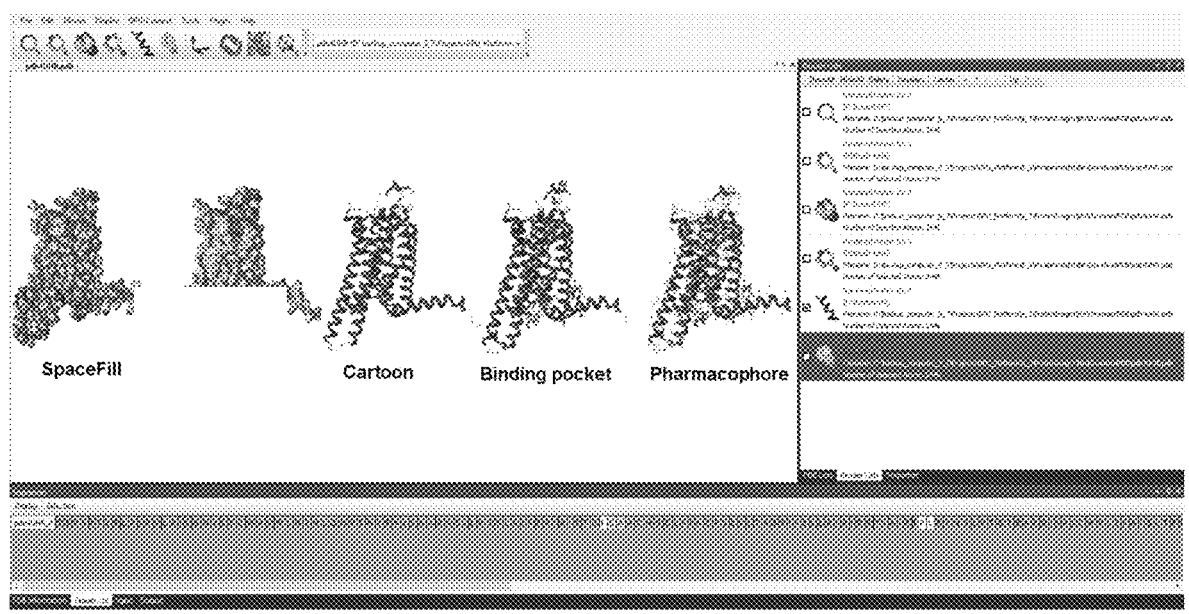
FIG. 2 illustrates a screen shot of a three-dimensional molecular model of a drug as displayed using a GPU-accelerated drug design and pharmaceutical application according to certain aspects of the present invention.
Figure 3:
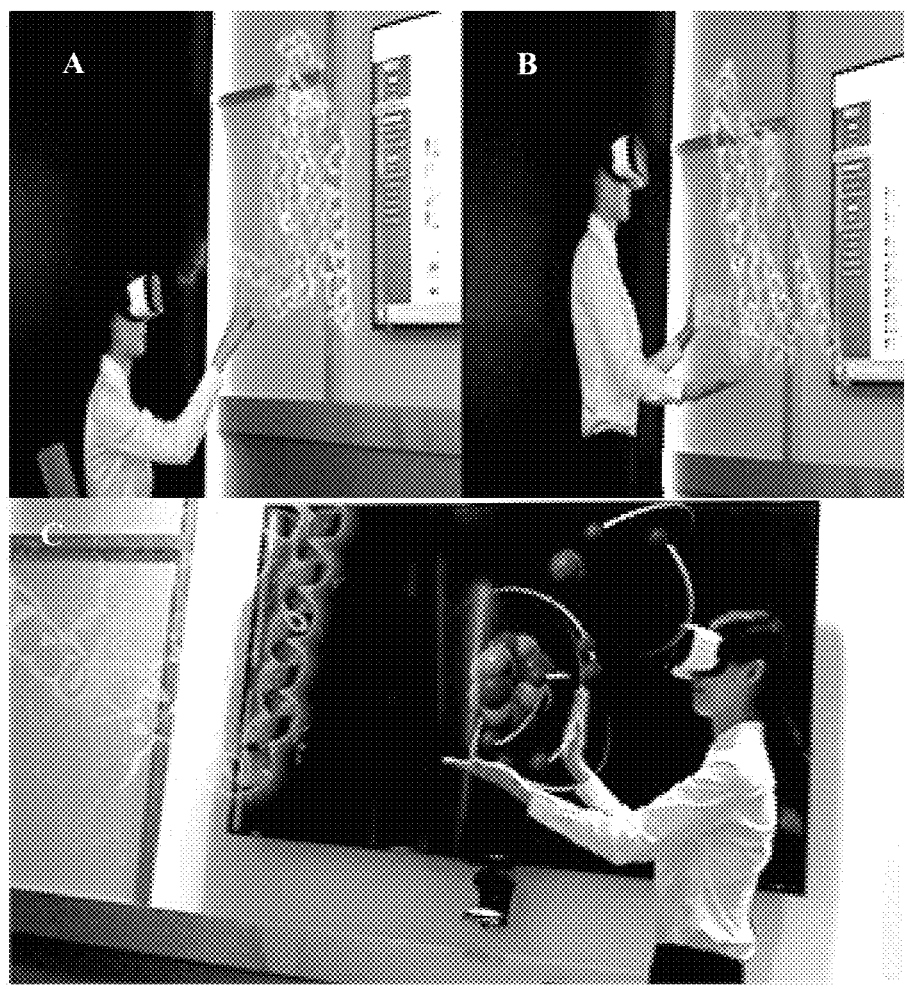
FIGS. 3A-3C are photographs of a user interacting with a GPU-accelerated drug design VR/AR/MR pharmaceutical applications according to certain aspects of the present invention.
Figure 4:
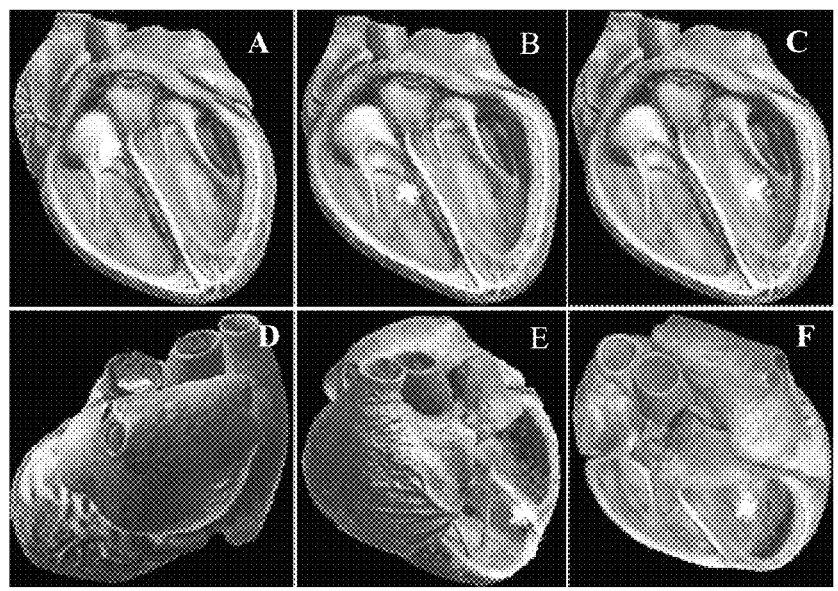
FIGS. 4A-4F illustrate screen shots taken from a VR/AR/MR visualization application for drug cardiovascular pharmacokinetic analysis in the heart according to certain aspects of the present invention.

(2) VR/AR/MR drug discovery application:

With reference to FIG. 2, the presently disclosed software application may provide 3D visualization, such as similar to PyMol, homology modeling, such as 3D structures, prediction of binding site(s), generating of pharmacophore models and pharmacophore filtering/screening, such as NCI molecular database (which includes 210,000 small molecules, screening completed within 1.5 hours), and protein-protein/protein-small molecule/protein-DNA docking, etc. This cross-platform application is developed based on the GPU accelerated technique of the present invention. Such visualization may assist in various aspects of drug discovery.

With reference to FIGS. 3A-3C, the presently disclosed invention may provide a VR/AR/MR software application based on an innovative means to display and interact with medical information, such as images of organs, body systems, or even whole bodies. In addition to 3D representations of proteins, DNA, small molecules such as drugs, etc., this software application may be designed to display data that includes 3D representations of single organs, clusters of organs, specific systems of the body (circulatory system, digestive system, nervous system, skeletal system, etc.), or the whole body.

The presently disclosed invention may provide a VR/AR/MR software application based on an innovative drug discovery platform with GPU-accelerated big data technology. The presently disclosed invention may be configured to function cross-platform. That is, the systems and methods may function on devices or platforms which include AR/MR devices (Microsoft HoloLens, Google Glass), VR devices (e.g., Oculus Rift), iOS, Android, and Microsoft Windows platforms. Users may be allowed to load, move, resize, rotate, delete, and stretch the holographic images by keyword commands or gestures (see FIGS. 3A-3C).

The software application may provide users with interactive operation. For example, the user may be provided with a view of another user's operation (e.g., a teacher or instructor), in addition to being allowed to operate/manipulate the 3D model under the authorization of the other user.

(3) VR/AR/MR precision medicine application:

The presently disclosed methods and systems provide a VR/AR/MR software application for a variety of precision medicine topics. For example, as shown in FIGS. 4A-4F, the presently disclosed systems and methods may provide drug pharmacokinetic and pharmacokinetic analysis in the heart and kidney. The software application includes VR/AR/MR visualization and big data mining and analysis, which may include: (i) applying software tools that predict potential pharmacological properties of compounds, (ii) carrying out molecular similarity searches, in which more than 75% similarity to the known drug(s) is considered as a potential small molecule with therapeutic potential, and (iii) performing in-silico high-throughput docking and evaluation. Positive results may be visualized on a VR/AR device such as HoloLens, or Google Glass, etc. FIGS. 4A-4F illustrate findings for a novel small molecule with potential therapy for heart disease, where individual panels show progress of the small molecule within the heart, as visualized on a VR/AR device using methods of the presently disclosed invention. Prediction of drug pharmacokinetics and pharmacokinetics in various other body organs and systems is also provided by the systems and methods disclosed herein.

Figures 5A, 5B:
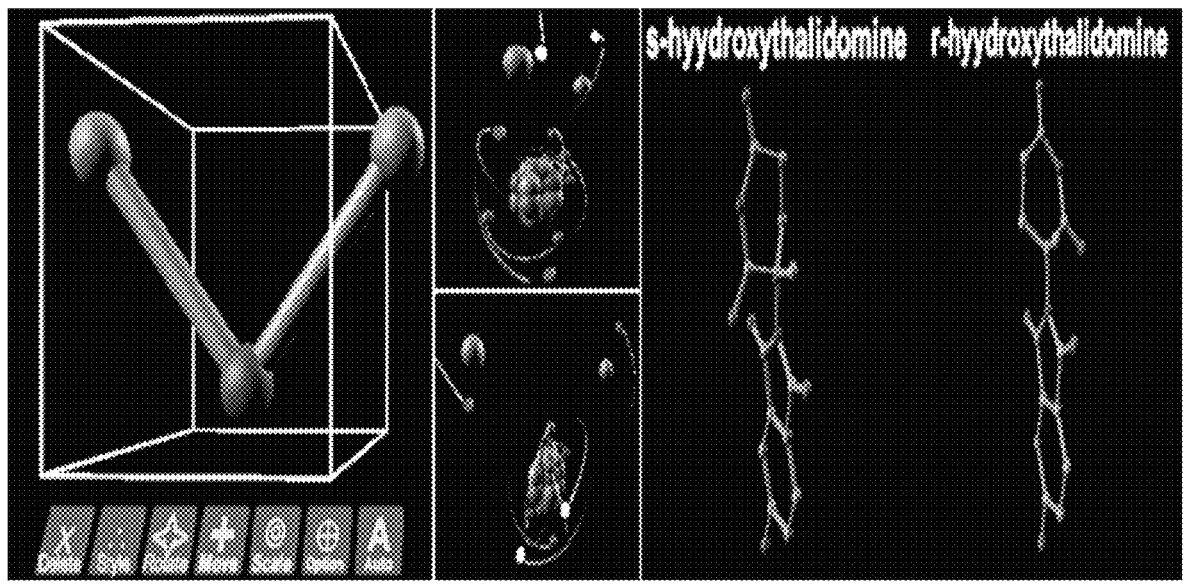
FIGS. 5A-5B illustrate screen shots taken from a VR/AR/MR quantum chemistry application according to certain aspects of the present invention.

(4) VR/AR/MR quantum chemistry application:

The presently disclosed methods and systems provide a VR/AR/MR software application that may (i) display the elementary electron orbital, (ii) display the shared electrons between different atoms as a function of time, (iii) calculate the chemical properties for various compounds, (iv) show the difference between the —S or —R configurations, and (v) display the chemical reaction safe with games, etc. For example, FIG. 5A shows the electron orbit of H and O, as well as their crystal structure, and FIG. 5B shows the difference between the —S or —R configurations of a small molecule.

Figures 6A, 6B:
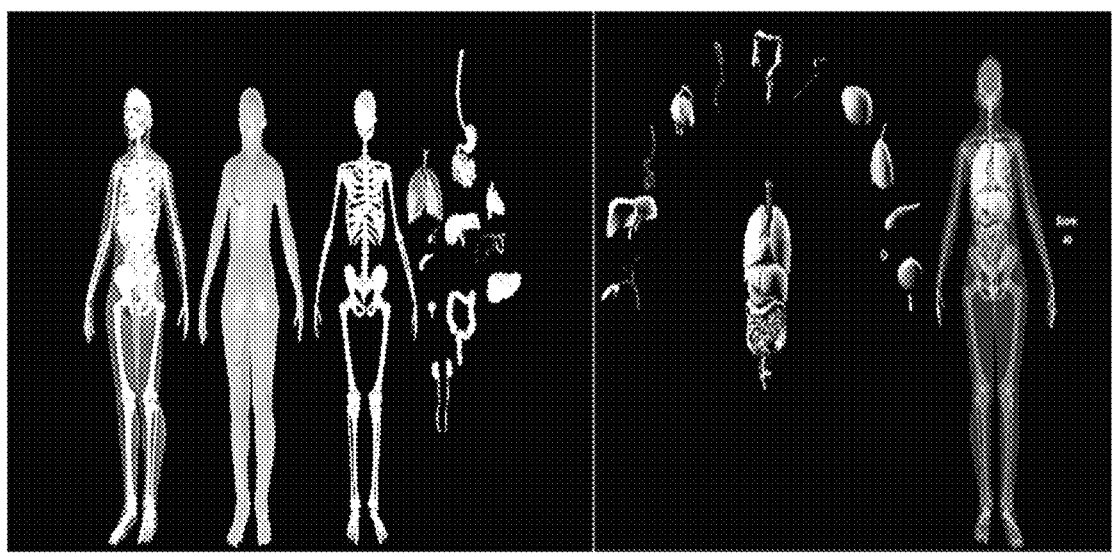
FIGS. 6A-6B illustrate screen shots of a VR/AR/MR organ/skeleton application according to certain aspects of the present invention.

(5) VR/AR/MR Organ (Skeleton) application:

As discussed above, the presently disclosed methods and systems provide a VR/AR/MR software application to display medical information such as images of organs, body systems, or even whole bodies based on data 3D imaging data (see FIGS. 6A-6B). The system may function to allow a user to: (i) select any organ/skeleton, (ii) move the organ/skeletons to the correct location, (iii) learn about the roles and functions of the various organs and systems, etc. The 3D imaging data may be collected from a range of medical technologies known in the art, such as magnetic resonance imaging (MRI), CAT scans, tomography, ultrasound, etc. This imaging data may be retrieved from an information server, or may be accessed in real time from an imaging procedure. The 3D imaging data may also be provided from computer graphic generated images based on known 3D information of organs, or other body systems.

(6) VR/AR/MR games, tutorials, learning applications:

The presently disclosed invention also provides software applications that may utilize any of the previously indicated 3D data or imaging methods, such as according to any of the systems and methods disclosed herein, configured as games. For example, the VR/MR/AR organ application may be configured as a game where the user receives points for correctly locating, identifying, placing the various organs or systems of the body in 3D space. The VR/MR/AR organ application may be configured to provide a means for practice surgery, so that a medical student may practice and/or a specific surgical technique. The presently disclosed invention envisions that any or all of the systems and methods disclosed herein may be configured as tutorials or exams. For example, the VR/MR/AR molecule application may be configured as an exam where the user receives points for correctly locating and identifying the various atom types, binding sites, —S or —R configurations, etc.

Figure 7A:
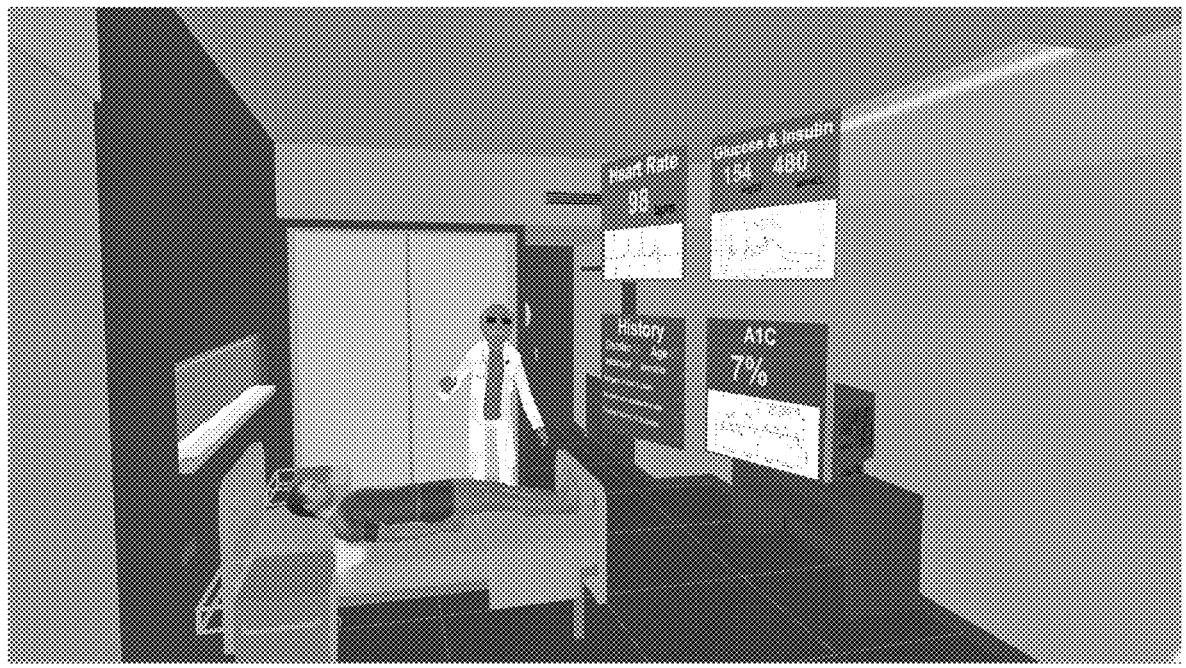
FIGS. 7A-7B illustrate screen shots taken from a VR/AR/MR "Holographic & Interactive 3D Diabetic" module for novel training and teaching in accordance with certain aspects of the presently disclosed invention.
Figure 7B:

(7) VR/AR/MR "Holographic & Interactive 3D Diabetic" for novel training and teaching:

The presently disclosed methods and systems also provide virtual reality and mixed reality 3D diabetic training and teaching applications (see FIGS. 7A-7B). FIG. 7A illustrates a virtual scenario that provides an electronic medical record which shows past medical records of a virtual patient, and the diagnosis results show the different indicators of the current virtual patient (derived from the virtual device test) and the results obtained therefrom. FIG. 7B illustrates a scenario wherein according to the previous results, it is concluded that the virtual patient was diagnosed as type II diabetes (with an AIC of 7% and a BMI greater than 25 kg/m2, etc.), and the treatment plan was: metformin+lifestyle management. These virtual scenes (people, equipment, furniture, etc.) can be directly touched, moved or otherwise manipulated. Teacher or students can act as a doctor during the simulation, and they can interact with the virtual patient, equipment, furniture, etc.

As detailed in the examples detailed above, the methods of the presently disclosed invention include a method for providing an augmented or virtual reality learning application, wherein the application may be executed by one or more processors. For example, the method may be embodied on a non-tangible computer readable medium tangibly embodying non-transitory computer-executable program instructions thereon that, when executed, cause a computing device to carry out the methods steps of the present invention.

Generally described, the method may decode a request for a data set related to a first target stored on an information server. As detailed, this data set generally includes information regarding spatial information of an arrangement of the first target in a physical environment, such as a three dimensional (3D) structure of the target. In addition to 3D structural information, the data set may include color, texture, and other information regarding a surface appearance of the target, such as for a target that is an organ or other body part. The method may then access, by a mobile internet device via a wired or a wireless network, the information server on which the 3D and other information may be stored. This information may be imported from the information server, and spatial information may be extracted from the data set. A 3D spatial image may then be displayed on the mobile internet device, wherein the spatial image is based on the spatial information.

According to certain aspects, the spatial information comprises a digital representation of an arrangement of the first target in a physical environment, such as in a current physical location of the user, or in a graphically generated environment.

According to certain aspects, a spatial image may be generated for one or more additional targets, and the method may further include altering the spatial image of the first and second, or additional, targets on the mobile internet device based on user commends. Such may be done to dock molecules relative to one another, such as a drug molecule docked within a binding site on a protein, or to dock an organ within a larger system of a body, such as docking internal organs in their proper locations in a body cavity.

II. Personalized Medical Tracking and Reminder Applications

The presently disclosed methods and systems also provide personalized medication scheduling, medical appointment scheduling, supporting holographic and interactive 3D representations of data sources. According to certain aspects, the software applications are configured to work across many platforms (e.g., iOS, Android, Microsoft Windows, etc.) to remind a user thereof to take and refill medications, or to schedule and attend medical appointments in a timely manner The presently disclosed software applications may use artificial intelligence (AI) and/or big data analysis algorithms for precision/personalized medication. Additionally, in conjunction with other technology and/or health companies, educational and/or medical institutions, the presently disclosed software application may import data which may be used to fine tune and improve the prescribing and other information sources.

The presently disclosed software application may further analyze the health data using an artificial intelligence (AI) and clinical data mining algorithm, which may include, but is not limit to: (i) recording, comparing, and analyzing the patient or user data before drug and after drug (long term) use, before and after different drugs or dosages, etc. The analysis may further compare the patient or user data with that of a population in order to provide and/or refine the schedule/plan for the patient or user medication dosage, dose schedule, and even drug type. As such, the presently disclosed software application may help the patient or user to manage their health data and plan.

Thus, the present invention includes a computer implemented method for providing a medication and/or appointment reminder. According to certain aspects, the method may comprise connecting to an information server via an internet protocol network; acquiring stored patient information from the information server, wherein the stored patient information comprises a medication to be taken by a patient and a dose schedule; starting a timer associated with the dose schedule; and activating an alert or alarm at a time interval defined by the dose schedule.

Acquiring the stored patient information may comprise accessing the information server having stored thereon a set of patient specific data. The set of patient specific data may comprise at least a patient name, a medication identification, and a medication dosing schedule. The set of patient specific data may further comprise a patient age, a patient weight, a patient height, a patient blood pressure, a patient cholesterol, a patient insulin level, a patient blood sugar level, a patient heart rate, a patient temperature, or any combination thereof.

The patient specific data may be obtained via direct input by the patient or user, and/or from a medical database maintained by the patient's or user's pharmacy or medical facility (e.g., primary care physician, hospital or medical facility, etc.), or may be information encoded on the medication (e.g., on a barcode or QRcode, such as on the label of the medication container).

Acquiring the stored patient information may further comprises accessing a second server, such as a server associated with a health or fitness tracker which may store thereon current values of a patient age, a patient weight, a patient height, a patient blood pressure, a patient cholesterol, a patient insulin level, a patient blood sugar level, a patient heart rate, a patient temperature, or any combination thereof. As such, the set of patient specific data may further comprise information stored on the second server.

The patient specific data may be used to determine a change to the dose schedule, or a health message regarding the dose schedule.

The method may further comprise sending reminders regarding an appointment schedule. As such, the stored patient information may further comprise an appointment schedule, and the method may further comprise starting a timer associated with the appointment schedule; and activating an alert or alarm at a time interval defined by the appointment schedule.

According to certain aspects of the method, the stored data may only comprise an appointment schedule, and the method may focus solely on alerts regarding that appointment schedule. That is, acquiring stored patient information from the information server, wherein the stored patient information comprises the appointment schedule; starting a timer associated with the appointment schedule; and activating an alert or alarm at a time interval defined by the appointment schedule.

The present invention further includes a system comprising a processor; and a memory containing instructions that, when executed by the processor cause the processor to execute any of the methods described herein.

The present invention further includes a computer implemented program product for providing a medication and/or appointment reminder, comprising a non-tangible computer readable medium tangibly embodying non-transitory computer-executable program instructions thereon that, when executed, cause a computing device to execute any of the methods described herein.

Figures 8A, 8B, 8C:
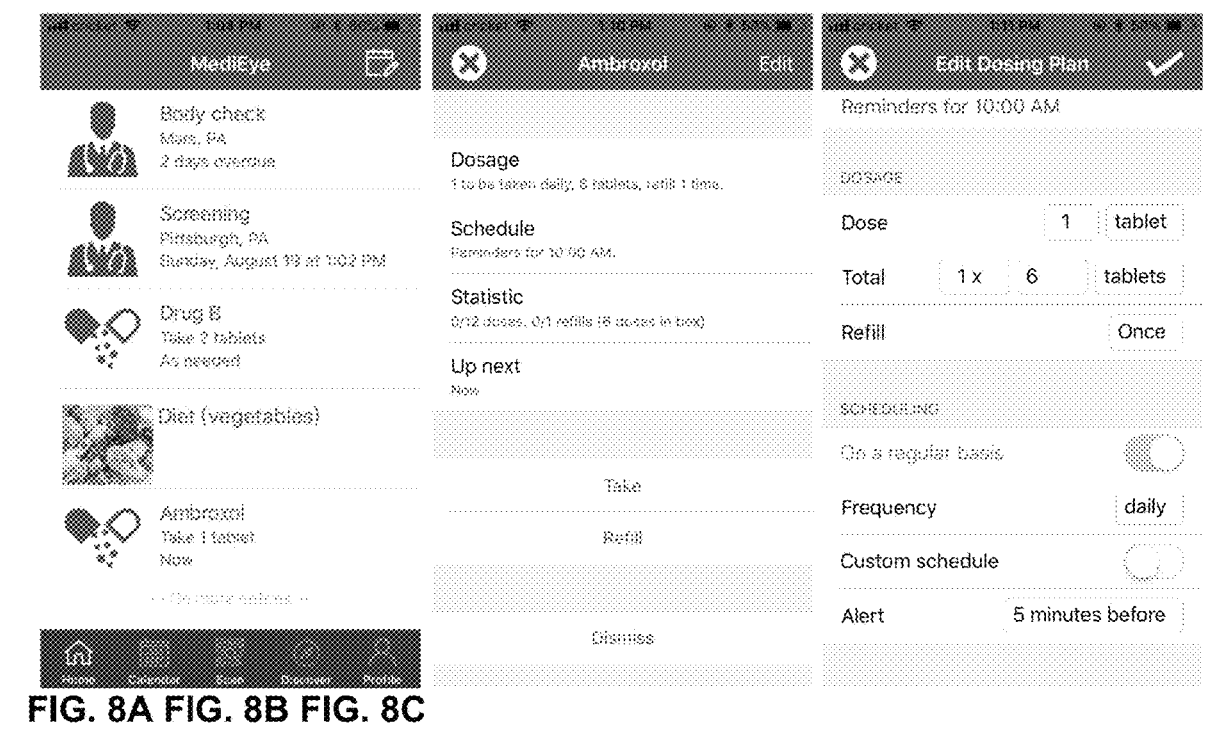

With reference to FIGS. 8A-8C (a prototype, named "MediEye"), the presently disclosed software application may provide medication (drug and diet) and appointment reminders. For example, if the current date and time are as shown in FIG. 8A (1:04 PM on Monday Aug. 16, 2018), it may be time for a specific patient or user to take their medication, Ambroxol in this example. When the patient or user clicks the Ambroxol region on the screen of a mobile device, with application "MediEye", for example, MediEye may redirect to detailed information as shown in FIG. 8B. The information may include a description of the "Dosage" (1 to be taken daily, 6 tablets, refill 1 time), "Schedule" (reminders for 10:00 AM), "Statistic" (0/12 doses, 0/1 refills {6 doses in box}), and "Up next" (now). The patient or user can click the "Take", "Refill" or the "Dismiss" button. "Refill" is to remind the patient or user to fill or refill this medication.

As used herein, the term "click" may be taken to indicate that a user of the application makes a selection by any of the known means in the art, such as direct contact with a button on a mouse or a portion of the screen that indicates the user's selection of a specific option (by touching the region on a touch sensitive screen, or by pointing at the region on the screen using the mouse, for example, and pushing the button on the mouse). The term "click" may also be taken to mean that the user has made a selection using eye or hand movements, such as eye movements when using a VR/AR device.

As shown in FIG. 8C, the patient or user may also be able to "Edit" the information stored in the software application MediEye. The contents available to the patient or user to change include "Dose" (how many tablets, pills, sprays, etc.), "Total Dose", "Refill times", "Frequency", "Custom Schedule" (on/off), "Alert time", etc.

Figures 9A, 9B, 9C:
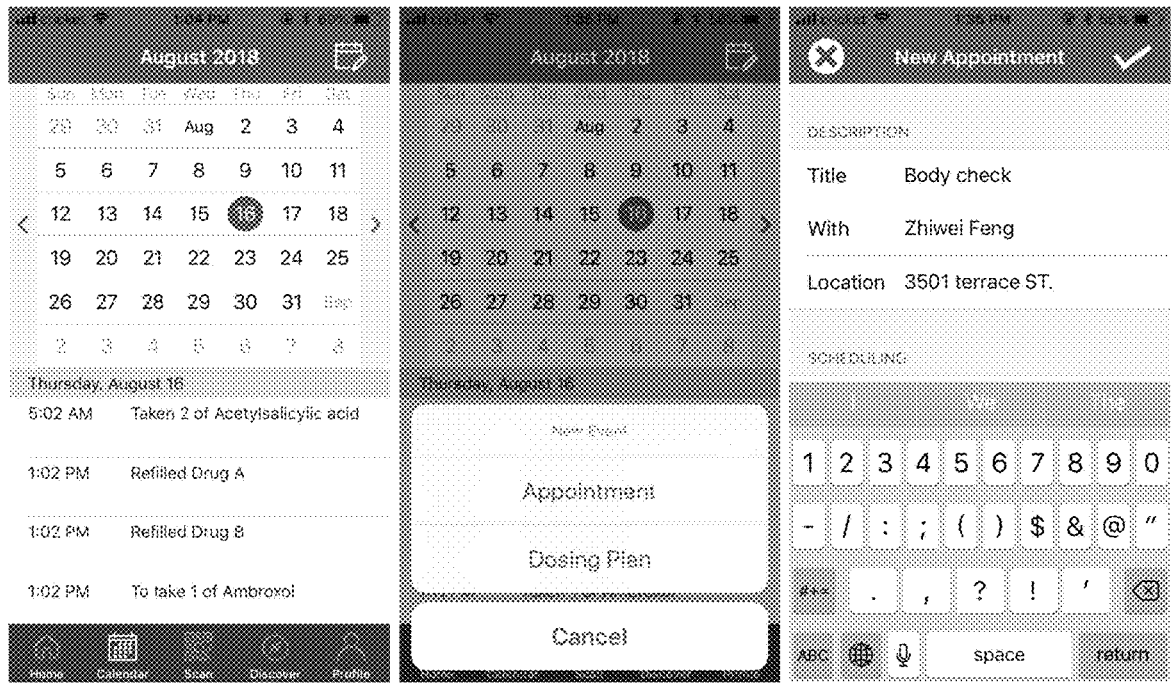
FIGS. 9A-9F illustrate exemplary screen views of a calendar interface of a software application in accordance with certain aspects of the presently disclosed invention.

With specific reference to FIGS. 9A-9F, events may be added/removed/edited on a "Calendar" which may be shown in a main ("Home") screen of the software application or may be shown on a separate screen of the application. For example, as shown in FIG. 9A, the current date/time is listed as "Today is Aug. 16, 2018 (Thursday)". The software application may highlight that date on a calendar as a default. The patient or user may be able to "Scroll left" the screen, at which point the software application may show an earlier month or week. The patient or user may also be able to "Scroll right" the screen to show a later month or week.

The patient or user may be able to add/edit/remove the new event(s)/reminders on today or a day in the future by selecting a specific day, as shown in FIG. 9B. For example, the patient or user may want to add a new appointment for body check on Aug. 19, 2018 at 1:40 P.M. The patient or user would first click the "Edit" logo on the right top of the screen, and then click the "Appointment" button.

Figures 9D, 9E, 9F:
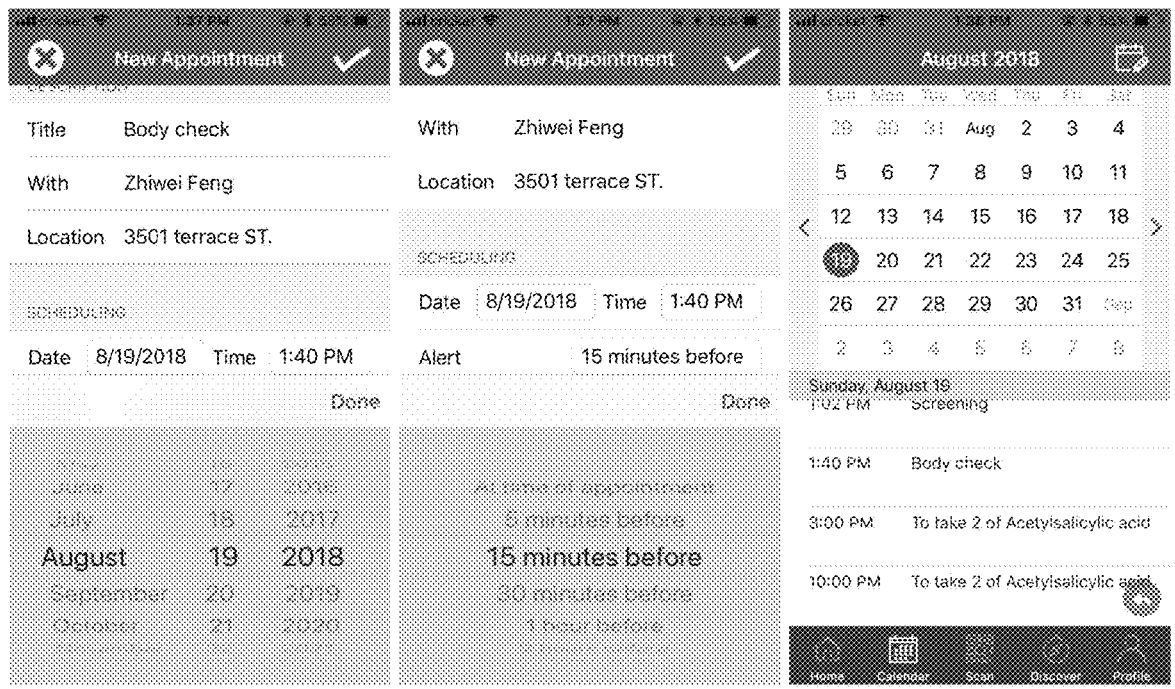

As show in FIG. 9C to FIG. 9E, screen shots of the software application MediEye, as installed on a smart phone, allow the patient or user may add the detailed information for this coming appointment (e.g., appointment on Aug. 19, 2018 at 1:40 P.M.). When done, the patient or user may click the "I" button on the right top, which redirects the application to the "Calendar" page, at which point the patient would select the day (e.g., click "19") assuming the correct month is selected (e.g., swipe right or left to select the appropriate month). The newly entered appointment is now visible on the calendar, as shown in FIG. 9F.

The software application of the present invention may also provide a means to set-up reminders for things such as medical appointments and/or drug schedules. For example, the presently disclosed software application may provide the patient or user with two ways to set up their reminders. In a first method, when a patient or user picks up their medications in the pharmacy, a pharmacy generated barcode or QRcode which may incorporate information specific to that patient or user may be included on the medication. Shown in FIG. 10A is an interface that may allow a patient or user to scan the barcode or QRcode.

The information from the scanned barcode or QRcode may include the patient's or user's name, date of birth, full list of medications or supplements, dosage, usage, etc. The barcode or QRcode, which may provide the additional information in an encrypted state which may use the patient's or user's date of birth and family name as the key (e.g., in an encryption algorithm) may be pushed to or scanned by patient's or user's mobile device using the presently disclose software application. Moreover, the software application may provide the detailed information of the prescription on the patient's or user's mobile device, as shown in FIG. 10B. For example, information for Morphine, including chemical structure, definition ("what is morphine"), side effects, warnings, instructions, drug to drug interactions, etc. may be provided. The software application may parse this patient or user information and the big data analysis algorithm may assist or help to set up the reminders.

Alternatively, the patient or user may manually set up the reminders. For example, the software application may set "August 16 (today)" as the default day, such as shown in FIG. 9A, but a patient or user may select any day they like. The presently disclosed software application may provide the medication/supplement names to avoid the wrong spelling, and the patient or user may be allowed to select various additional scheduling options. For example, one option may be to "avoid bed time" to take a medication, and the schedule may incorporate that scheduling restriction into the overall drug/appointment schedule. The presently disclosed invention further provides several optimum plans after analysis of all of the data and restrictions using the big data analysis.

Figures 10A, 10B, 10C:
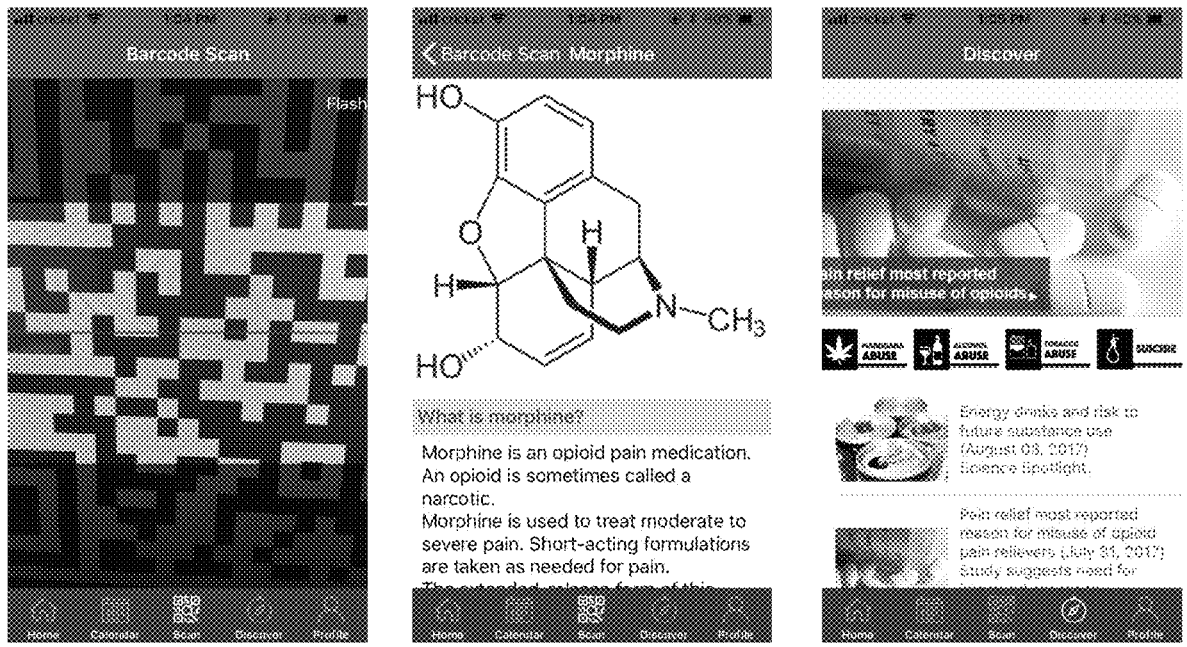
FIGS. 10A-10B illustrate exemplary screen views of a barcode/QRcode scan interface of a software application in accordance with certain aspects of the presently disclosed invention.
FIG. 10C illustrates an exemplary screen view of a news and information interface of a software application in accordance with certain aspects of the presently disclosed invention.

With specific reference to FIG. 10C, the patient or user may view the latest news and information on drug use and/or abuse in "Discover". For example, the patient or user may use the expanded NLP portion of the presently disclosed software application to display the latest news on drug use and/or abuse. This may be for the drugs currently prescribed to the patient or user, or for drugs which are closely related. Moreover, the patient or user may request such information on any drug or supplement of interest. Such may be accomplished via a web crawler program which may be integrated with, or may be a component of, the presently disclosed software application.

This news content may be vetted for reliability and/or priority may another program component which may be integrated with, or may be a component of, the presently disclosed software application. Additionally, the NLP algorithm may be used for abstractive sentence summarization. The presently disclosed software application may display the news or information as shown in FIG. 10C.

The presently disclosed software application may also provide a means to input patient or user profile information. This information may be entered directly by a user through interactions with the application. For example, at the beginning of a session (e.g., first use of the application), the patient or user may or may not be required to create an account. When required to create an account, such as when the presently disclosed software application has acquired enough users, each patient or user may enter specific personal information. Several different interfaces related to "Profile", such as "Sign in", "Create an Account", "Account Finder", "Profile Manage", "Name", "Image", "Allergic History", "Sleep Quality", "Health Condition", "Medication Summary", etc., may be a part of the presently disclosed software application.

Alternatively, or in addition, the patient or use information may be obtained from a data source, such as a health care provider. This information may be provided via the health care provider's servers.

Figure 11:
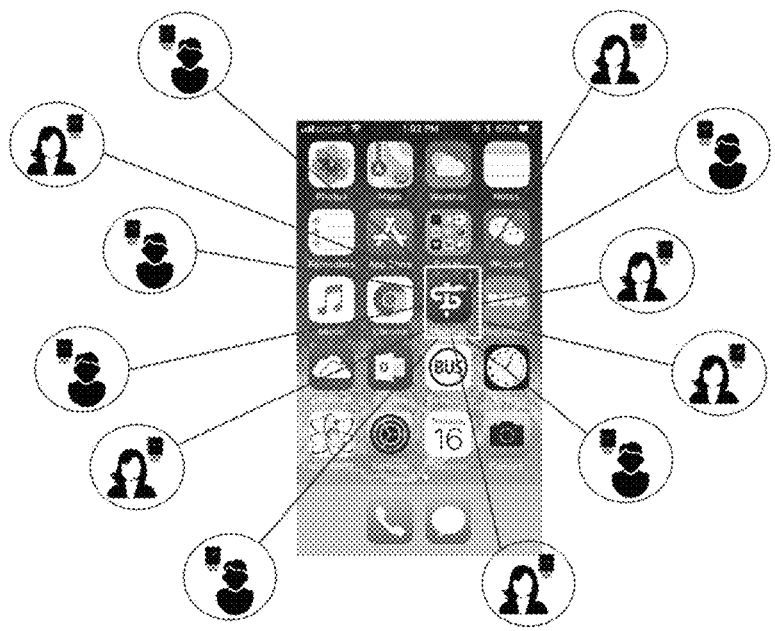
FIG. 11 illustrates an exemplary screen view of a health data, health tracker input/review interface of a software application in accordance with certain aspects of the presently disclosed invention.

With reference to FIG. 11, the presently disclosed software application may also provide a patient or user with the ability to connect with a variety of resources. For example, beyond the medication and appointment reminders, the presently disclosed software application may connect to the patient's or user's fitness or health trackers (e.g., Apple Watch, Jawbone, Fitbit, Body Cardio, etc.). The patient or user may be allowed to sync their data to the presently disclosed software application, such as by "clicking" or "selecting" or touching that portion of the display (e.g., by clicking "sync devices"), after which their data may be synchronized through Wi-Fi or Bluetooth. The health data may include, but is not limit to, a user id (generated by the software application of the fitness or health tracker device), the patient or user age, sex, weight, temperature, heart rate, blood pressure (Body Cardio, Nokia), etc., in addition to the medication data already resident in the presently disclosed software application. In order to be compatible with more devices, the presently disclosed software application may utilize algorithms which may be designed to deal with different data with different formats.

The presently disclosed software application may assist the patient or user in generating (e.g., new users/patients) or refining their plan. As such, the patient or user data may be synced (automatically or by the patient or user to a server (e.g., cloud or server associated with the software application). The patient or user health data may be submitted and analyzed by an artificial intelligence (AI) segment of the presently disclosed software application, and/or clinical data mining algorithms.

The server may provide functions which include, but are not limit to: recording, comparing, and/or analyzing the patient or user data. The presently disclosed software application may first compare the patient's data between "before drug" and "after drug" (long term), including heart rate, blood pressure, temperature etc. Statistics may be generated which may show the patient's values versus those of the population (e.g., general population or the population on the same drug). If the patient's values are found to be outside of a standard range (e.g., higher than the maximum value in a population; or lower than a minimum value in a population), or to have varied greatly from a previously recorded value, the presently disclosed software application may provide the patient or user with a recommendation, such as "You may overdose, contact you doctor(s)", "You may see your doctor to change the dosage or add other medications", or the software application may show you some alternative dosing times/schedules by searching trends in similar patient(s).

While specific embodiments of the invention are described in detail within this document, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A method for providing an augmented or virtual reality learning application, the application executed by one or more processors, the method comprising:
   decoding a request for a first data set related to a first target stored on an information server;
   accessing, by a mobile internet device via a wired or a wireless network, the information server;
   importing the first data set from the information server;
   extracting a first spatial information from the first data set using a graphics processing unit of the mobile internet device;
   decoding a request for a second data set related to a second target stored on the information server, wherein the second target is related to the first target;
   accessing, by the mobile internet device, the information server;
   importing the second data set related to the second target from the information server;
   extracting a second spatial information from the second data set related to the second target;
   displaying a three-dimensional (3D) spatial image on the mobile internet device, wherein the spatial image is based on the first and second spatial information, wherein the spatial information comprises a digital representation of an arrangement of the first target and the second target, respectively, in a physical environment; and
   altering the spatial image of the first target, the second target, or both of the first and second targets on the mobile internet device based on user commands, wherein altering the spatial image includes moving the spatial image, resizing the spatial image, rotating the spatial image, deleting part of or all of a spatial image, stretching the spatial image, and any combination thereof.

2. The method of claim 1, wherein the first target comprises an organ, a nervous system, a digestive system, a circulatory system, or a combination thereof, and the second target comprises a skeleton, a body, or combination thereof, wherein the method further comprises:
   altering the spatial image of the first target relative to the second target.

3. The method of claim 2, wherein the organ comprises a single organ, multiple organs, or an entire body.

4. The method of claim 1, wherein the first target, the second target, or both of the first and second targets comprise a molecule, wherein the molecule is a protein molecule, a DNA molecule, an RNA molecule, a peptide, a carbohydrate, a lipid, a drug, or a combination thereof, and wherein the method further comprises:
   altering the spatial image of the first target relative to the second target.

5. The method of claim 4, wherein the data set related to the first target, the second target, or both of the first and second targets comprise a crystallographically determined 3D structure of a protein molecule, a DNA molecule, an RNA molecule, a peptide, a carbohydrate, a lipid, a drug, or a combination thereof.

6. The method of claim 2, wherein the data set related to the first target, the second target, or both of the first and second targets comprise a reconstruction from an imaging method selected from the group consisting of: a CT scan, a PET scan, a MRI, a tomographic MRI, an ultrasound, and an ultrasound tomography.

7. The method of claim 1, wherein the mobile internet device comprises at least one of the following: a game device, a smart phone, a tablet, a camera, a robot, an augmented or virtual reality viewer, and a watch.

8. The method of claim 1, wherein the user commands comprise hand gestures or eye movements that are recognized by a camera of the mobile internet device.

9. A computer implemented program product for providing an augmented or virtual reality learning tool, comprising computer-executable program instructions that, when executed, cause a graphics processing unit (GPU) of a computing device to implement the method of claim 1.

10. The method of claim 4, wherein the first target is a drug or a protein molecule, and the second target is a protein molecule, a DNA molecule, an RNA molecule, a peptide, a carbohydrate, or a lipid, and wherein altering the spatial image of the first target relative to the second target comprises docking the first and second targets together, and wherein the method further comprises:
    displaying binding pockets, pharmacophores, or both in solid, transparent, or dotted modes.

11. The method of claim 10, further comprising:
    displaying interactions between the first and second targets when docked, wherein the interactions comprise H-bonding, van der Waals, charge-charge, hydrophobic interactions, or any combination thereof.

12. A computer-implemented method for providing a medication and/or appointment reminder, the method comprising:
    connecting to an information server via an internet protocol network;
    acquiring stored patient information, wherein the stored patient information comprises a medication to be taken by a patient and a dose schedule;
    starting a timer associated with the dose schedule; and
    activating an alert or an alarm at a time interval defined by the dose schedule, wherein acquiring the stored patient information further comprises accessing a second server having stored thereon a current value of a patient age, a patient weight, a patient height, a patient blood pressure, a patient cholesterol, a patient insulin level, a patient blood sugar level, a patient heart rate, a patient temperature, or any combination thereof.

13. The computer implemented method of claim 12, wherein the stored patient information obtained from the second server are used to determine a change to the dose schedule, or a health message regarding the dose schedule.

14. The computer implemented method of claim 12, wherein acquiring the stored patient information comprises accessing a QRcode or barcode on a medication container or pamphlet.

15. The computer implemented method of claim 14, wherein the stored patient information obtained from the second server are used to determine a change to the dose schedule, or a health message regarding the dose schedule.

16. The computer implemented method of claim 12, further comprising:

accept, from a user, a query regarding the medication or a second medication or supplement, wherein the method uses a natural language processing algorithm to display current information regarding the medication, second medication, or supplement on a user device, wherein the current information includes one or both of drug-drug interactions and side effects.

17. A computer-implemented method for providing a medication and appointment reminder, the method comprising:
   accept input from a user comprising patient specific information and an appointment schedule, and store the input on a first server, wherein the patient specific information comprises a patient age, a patient weight, a patient height, a patient blood pressure, a patient cholesterol, a patient insulin level, a patient blood sugar level, a patient heart rate, a patient temperature, or any combination thereof;
   accept input of at least one medication to be taken by a patient and a dose schedule for the medication;
   start a timer associated with the dose schedule;
   activate a medication alert or alarm at a time interval defined by the dose schedule for the medication, and an appointment alert or alarm defined by the appointment schedule; and
   display current information about the at least one medication on a user device, wherein the current information about the at least one medication includes interactions of the medication with other drugs, side effects, or both interactions of the medication with other drugs and side effects.

18. The computer-implemented method of claim 17, further comprising:
   accept, from the user, a query regarding the medication or a second medication or supplement, wherein the method uses a natural language processing algorithm to display the current information regarding the medication, second medication, or supplement on the user device.

19. The computer-implemented method of claim 17, wherein the input of the medication to be taken by the patient and the dose schedule for the medication is provided by the user.

20. The computer-implemented method of claim 17, wherein the input of the medication to be taken by the patient and the dose schedule for the medication is from a QRcode or barcode on a medication container or pamphlet.

21. The computer-implemented method of claim 17, wherein the input of the medication to be taken by the patient and the dose schedule for the medication is from a health care provider.

22. The computer-implemented method of claim 17, further comprising:
   acquire current patient information from a second server, wherein the current patient information comprises a current value of the patient weight, the patient blood pressure, the patient cholesterol, the patient insulin level, the patient blood sugar level, the patient heart rate, the patient temperature, or any combination thereof,
   wherein current patient information obtained from the second server is used to determine a change to the dose schedule, or a health message regarding the dose schedule.

* * * * *